United States Patent [19]
Dobbs et al.

[11] Patent Number: 5,550,886
[45] Date of Patent: Aug. 27, 1996

[54] X-RAY FOCAL SPOT MOVEMENT COMPENSATION SYSTEM

[75] Inventors: John Dobbs, Hamilton; Ruvin Deych, Brookline, both of Mass.

[73] Assignee: Analogic Corporation, Peabody, Mass.

[21] Appl. No.: 343,240

[22] Filed: Nov. 22, 1994

[51] Int. Cl.⁶ .................................................. G01N 23/00
[52] U.S. Cl. .................................................. 378/19; 378/4
[58] Field of Search ............................................ 378/19, 4

[56] References Cited

U.S. PATENT DOCUMENTS

| | | |
|---|---|---|
| 3,778,614 | 12/1973 | Hounsfield . |
| 4,145,610 | 3/1979 | Perilhou . |
| 4,547,893 | 10/1985 | Gordon . |
| 4,769,827 | 9/1988 | Uno et al. . |
| 4,991,189 | 2/1991 | Boomgaarden et al. ............... 378/19 |
| 5,228,069 | 7/1993 | Arenson et al. . |

Primary Examiner—Craig E. Church
Attorney, Agent, or Firm—Lappin & Kusmer LLP

[57] ABSTRACT

An apparatus for compensating for drift of the focal spot of an X-ray radiation source used in a tomography system is disclosed so as to maintain a primary collimated beam of radiation emanating from the focal spot aligned with target detectors of the tomography system. A second collimated beam of radiation is produced from the same focal spot and directed along a different axis from the first beam. An array of detectors track the movement of the second collimated beam and produce signals which are used to reposition the collimator used to collimate the primary beam so as to maintain the primary beam substantially aligned with the target detectors.

25 Claims, 6 Drawing Sheets

X-RAY FOCAL SPOT MOVEMENT COMPENSATION SYSTEM

RELATED APPLICATION

This application is related to U.S. Ser. No. 08/343,248, contemporaneously filed with the present application in the names of John Dobbs and Hans Weedon, entitled X-ray Image Data Normalization in a CT Scanner, and assigned to the present assignee (Attorney's Docket Number ANA-60).

1. Field of the Invention

The invention relates generally to tomography systems, and more particularly to an apparatus for maintaining the alignment of a collimated beam of radiation in a tomography system so as to (a) compensate for Z-axis focal spot shift and (b) maintain the positional stability of the beam on detectors of the tomography system.

2. Background of the Invention

Tomography systems have been used for many years to create images of cross-sectional slices through objects, and are particularly useful as a diagnostic aid. The most commonly known form is the CT (computerized tomography) scanner. The third generation type of CT scanner includes a disk or drum, rotatably supported in a gantry support frame and supporting an X-ray source and an X-ray detector array. Typically, the radiation source provides either periodic X-ray pulses or continuous-wave (CW) X-rays. The X-rays emanate from a point usually referred to as the "focal spot". A collimator is provided to control the shape and the direction of the X-ray beam from the focal spot. The detector array, usually comprising gas or solid state detectors for counting X-ray photons, is disposed on the disk at a predetermined position diametrically opposite to the source on opposite sides of an opening in the disk (through which the object being scanned is disposed) so as to define a corresponding plurality of X-ray paths from the source and collimator to the respective detectors within a common plane of rotation of the disk. The ray paths between the focal spot and the detectors resembles a fan, and hence the term "fan beam" is sometimes used to refer to the shape of the beam.

In the fourth generation type CT scanner, the rotatable disk supports the X-ray source. However, the detectors are disposed on the gantry support frame, which rotatably supports the disk. The detectors are distributed around the support frame at predetermined angular spacings relative to the center of the disk so as to define a corresponding plurality of X-ray paths from the source to the respective detectors within a common plane of rotation of the disk. As the source rotates about the rotation axis of the disk, the ray paths from the rotating source to each detector resembles a fan beam with respect to each detector in which the point of convergence of the fan beam is the detector.

In either type of CT scanner, the disk is normally adapted to rotate through at least a full 360 degree rotation about a rotation axis, sometimes referred to as the "Z-axis", so that the source (and in the case of third generation machines the detectors) rotates through a plurality of incremental positions where a corresponding series or set of readings (called "projection views") by the detectors are made. The number of photons absorbed along the various ray paths through the object, during each sampling period defining each projection view, is a function of the absorption characteristics of the portions of the object along each path during each set of readings. Thus, a plurality of projection views are taken through the portion of an object disposed within the common plane of rotation of the X-ray paths (hereinafter the "scanning plane"). The detectors generate a corresponding plurality of analog information signals representative of X-ray flux detected by the detectors during each sampling period or projection view.

The output analog information signals of the X-ray detectors acquired from all of the projection views of the 360 degree rotation, i.e., through all of the incremental angular positions of the 360 degree rotation within the plane of rotation, are processed, typically through a back projection processing technique, so as to create a reconstructed image of the interior structure of the object exposed to the X-rays, typically in the form of a two-dimension image of a thin slice.

Great success has been achieved in the development of components, i.e., sources and detectors, for providing data based upon accurately measured X-ray flux during each projection view, as well as improved data acquisition systems (DASs) for processing the analog information signals provided from the detectors. The benefits of these developments include reduced electrical artifact-producing errors, such as gain error, systematically-related radial or displacement-related errors, electrical noise caused by electrical and encoding quantization noise, offset and gain variations, differential non-linearity of encoding devices and dielectric absorption effects, among others.

However, even employing such elaborate electrical compensation schemes, errors can still arise due to mechanical misalignments which occur during a scan, or over a number of scans. These errors can be critical when one considers that the image generation through CT scanning by the back projection method is based upon mathematical relationships first developed by Johann Radon. The standard CT scanning system, based upon these mathematical relationships, assumes that the components of the system, especially the source and detectors, always remain perfectly aligned relative to one another during a scan, both throughout each scan and over the course of many scans, and that the components move about an axis of rotation, the Z-axis, so as to circumscribe a "perfect" circle in the scanning plane, concentric with the intersection point of the rotation axis with the rotation plane, so as to define a "phantom image" of all mass disposed in the circle in the scanning plane.

The back projection process of reconstructing the phantom image is based on reconstructed values derived as a function of the measured data values obtained during each projection view of the scan. Thus, the image data acquired during the scan of the circular phantom image can be used to reconstruct the phantom image including the portion of any object in the flux path within the plane of rotation. It should be clear that the X-ray flux measurements themselves must be made extremely accurate relative to each other throughout each scan. Otherwise, systematic or random errors can prevent the determination of the reconstructed values to the degree of accuracy necessary to achieve a reconstructed image to the desired level of quality.

Consequently, any mechanical misalignments and lateral movement of the various tomography components during a scan, or those occurring over several scans (which are not correctable using current electronic error correcting techniques) can cause major inaccuracies in reconstructed images. Such images are misleading in their apparent information content and could lead to improper diagnosis by a physician relying on the data. These types of errors can destroy the integrity of the reconstructed image so as to make proper analyses very difficult, if not impossible.

One particular cause of misalignment is the source of the radiation itself. For example, in one type of X-ray source, the X-rays are generated by directing an electron beam at a tungsten anode. To aid in heat dissipation and to avoid melting, the anode, in the form of a disk, is continuously rotated through the path of the electron beam such that only a small portion of the disk is exposed to the electron beam at anyone instant of time. It is this small portion of the disk where the disk is exposed to the election beam that defines the focal spot or emanation of the high energy photons. A collimator containing a beam defining slit is typically positioned near the focal spot and relative to the detectors so that the X-ray beam defined by the slit will be aligned with the detector array. However, as the rotating disk anode heats up, thermal expansion causes the focal spot to shift, thus causing the path of the X-ray beam defined by the collimator slit to positionally drift with respect to the collimator and detectors. Typically, the rotational axis of the anode disk is perpendicular to the scanning plane and parallel to the Z-axis, and therefore any shift in the anode disk, hereinafter called "Z-axis beam shifting", causes a drifting or shift of the focal spot in a direction parallel to the Z-axis so that the X-ray beam shifts relative to the Z-axis. This shift means that not all of the X-ray flux emanating from the focal spot and passing through the slit of the collimator will necessarily be detected by each detector of the detector array, both because of the resulting spatial misalignment of the focal spot relative to the slit and detector array, and because of variations in the sensitivity of the detectors of the detector array in the Z-axis direction. This shift therefore can detract from the integrity of the image data and can cause major inaccuracies in the reconstructed image.

OBJECTS OF THE INVENTION

Accordingly, it is a general object of the present invention to provide an improved tomography system.

It is another, more specific object of the present invention to provide an improved apparatus for providing a more positionally stable beam of high energy X-ray photons used in a tomography system.

Another object of the present invention is to provide an improved X-ray radiation source assembly for use in a tomography system adapted to compensate for shifting of the focal spot of the X-ray source.

A further object of the present invention is to provide an improved tomography system which compensates for misalignment of the source relative to the collimator and detectors due to Z-axis beam shifting so as to provide more accurate scan data.

And another object of the present invention is to provide an improved source of X-rays which automatically compensates for the shifting of the focal spot of the radiation source so as to maintain alignment of the focal spot with respect to the collimator and detectors of a tomography system.

Yet another object of the present invention is to compensate for Z-axis focal spot shift and maintain the positional stability of the beam on the detector array in order to reduce errors in X-ray flux measurement due to variation in sensitivity of the detectors of the detector array in the Z-axis direction.

SUMMARY OF THE INVENTION

These and other objects of the present invention are achieved by a system for controlling the direction of the X-ray beam of a tomography system relative to collimator and the X-ray detector array of the tomography system so as to compensate for any shift of the focal spot in a direction parallel to the Z-axis so that the focal spot, collimator and the detectors remain aligned with one another.

In accordance with the preferred embodiment, the system includes a source of radiation for defining a focal spot from which a beam of radiation emanates, a monitoring device for detecting a shift of the focal spot in a direction parallel to the Z-axis, and an actuating device, preferably including a primary X-ray collimator, for adjusting the direction of the beam in response to a shift of the focal spot along an axis parallel to the Z-axis, hereinafter the "Z'-axis", as determined by the monitoring device so as to maintain the focal spot, primary collimator and detector array of the tomography system aligned.

This is preferably achieved by defining at least two beams of radiation from the focal spot of the source. Both beams preferably emanate from the same focal spot of the X-ray source. A primary beam of radiation is used to perform the scanning function of the tomography system, and is directed along a primary axis in the scanning plane through the object being scanned to the primary detector array of the tomography system. A secondary beam of radiation is directed at an angle with respect to the first beam, preferably in a direction transverse to the scanning plane, to a secondary monitoring device which monitors the position of the focal spot of the source of the beam along the Z'-axis. The secondary monitoring device preferably includes means for generating a position signal representative of the position of the focal spot along the Z'-axis. The monitoring device determines, in response to the position signal, if the focal spot has shifted along the Z'-axis, and sends any necessary control signals to the actuating device so as to move the primary collimator and adjust the direction of the primary beam in order to insure that the primary beam is correctly aligned with the primary X-ray detector array.

In a typical third generation tomography system, the primary beam is defined by the primary collimator, usually in the form of an X-ray impervious plate having a narrow elongated slit so as to define a fan beam emanating from the focal spot and increasing in width as the distance from the focal spot increases. The thickness of the slice defined by the beam to which the scanned object is exposed where the beam intersects the primary detector array is determined by (i) the width of the narrow slit of the primary collimator, and (ii) the spacings between the focal spot, primary collimator and the detector array. The width of the slit is much smaller than both the length of the slit and the diameter of the circle circumscribed by the X-ray source as it rotates about the Z-axis of rotation of the disk, e.g., the ratio of the slit length: slit width can vary from about 40 to 200. Typically, the thickness of the beam is less than about 10 mm, although this can vary.

The preferred system also includes a second collimator which forms the shape of the secondary beam and directs it onto the secondary monitoring device. As the focal spot shifts along the Z'-axis, the position of the secondary beam on the secondary monitoring device also shifts. The secondary monitoring device produces an output control signal representative of the amount and direction of the shift along the Z'-axis. The actuating element moves the primary collimator, in response to the control signal, to maintain the alignment of the focal spot, primary collimator, and the detector array of the tomography system, and thus, compensate for Z-axis beam shifting.

As described in copending U.S. Ser. No. 08/343,248, contemporaneously filed with the present application in the names of John Dobbs and Hans Weedon, entitled X-ray Image Data Normalization in a CT Scanner, and assigned to the present assignee (Attorney's Docket Number ANA-60), the secondary monitoring device can also be used to monitor the level of X-ray flux generated by the X-ray source, so that the secondary monitor device can be used to control the output of the radiation source and/or to provide compensation data when reconstructing the phantom image.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE DRAWINGS

Figure 1:
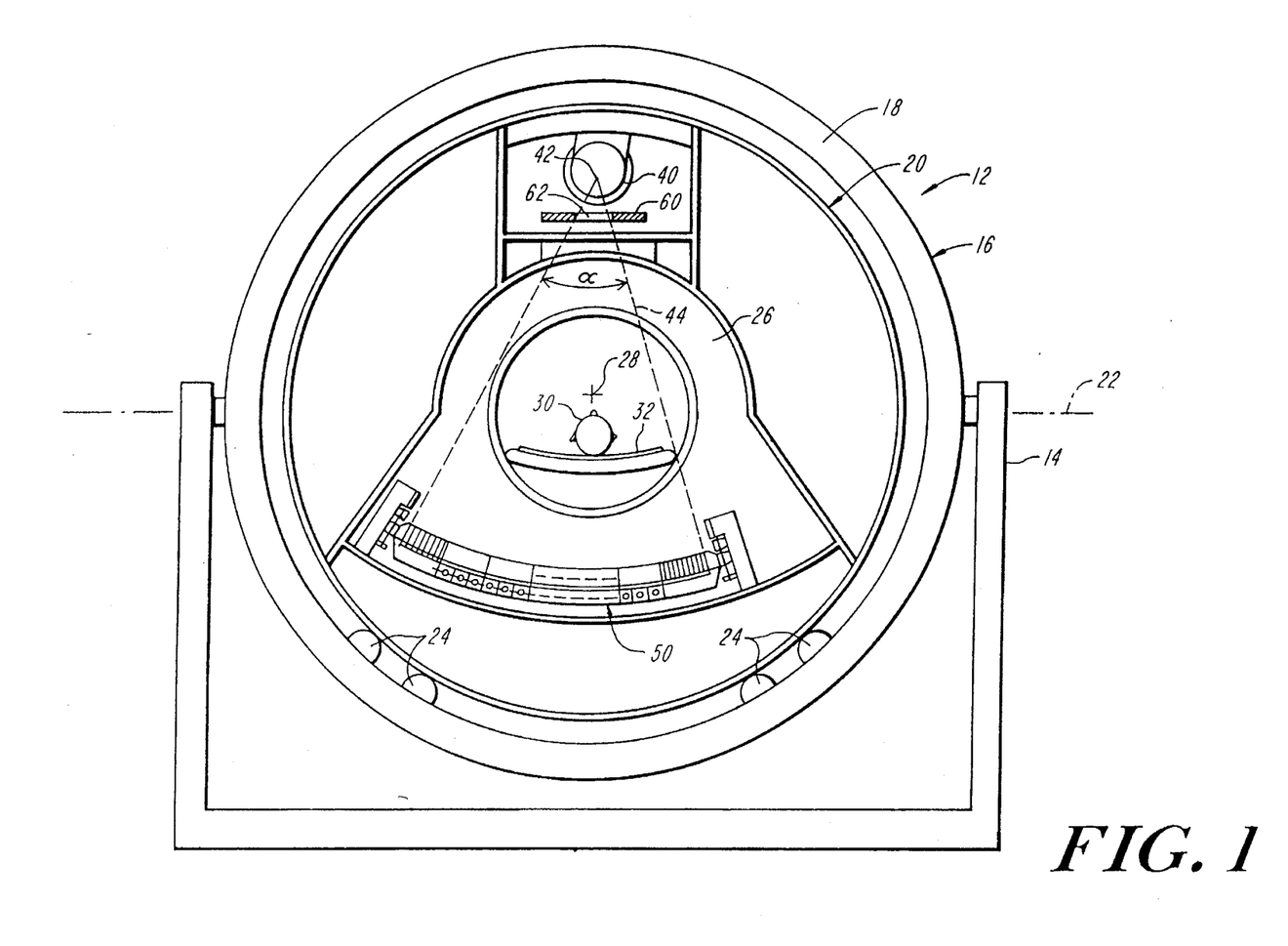
FIG. 1 is an axial view of a CT scanning apparatus employing the preferred embodiment of the present invention.

FIG. 1 shows a third generation type CT scanning apparatus 12, modified in accordance with the present invention. Apparatus 12 includes a support structure comprising a cart 14 for supporting a gantry assembly 16 including a cylindrical or annular support frame 18 and a rotatable disk 20 rotatably supported in the frame 18 for rotation about the Z-axis, indicated at 28. The support frame 18 can be pivotally mounted on the sides of cart 14 so as to permit adjustment of the orientation of the support frame 18 about the pivot axis 22. A suitable drive system, including drive rollers and idler rollers indicated at 24, for supporting and rotating the disk 20, is shown and described in greater detail in U.S. patent application Ser. No. 08/193,783, entitled X-Ray Tomographic Scanning System filed Feb. 8, 1994 in the name of Gilbert W. McKenna, and assigned to the present assignee (Attorney's Docket Number ANA-30). The disk 20 includes a circular opening 26 large enough for the torso of a patient 30, supported on a patient pallet 32, to pass through. The disk 20 also carries a source 40 of high energy X-ray photons and defining a focal spot 42 from which the photons emanate. The source is positioned on one side of the opening 26, while an array of primary detectors 50 are positioned opposite the source 40 for detecting X-ray photons received from source 40. The array of detectors are arranged in an arc having a center of curvature coincident with the focal spot 42. The disk can also carry energy sources and other support systems (not shown) necessary for performing the scanning function, as is well known, and as described for example, in U.S. patent application Ser. No. 08/193,696, entitled Tomographic Scanner Having Center of Rotation for All Physics filed Feb. 8, 1993 in the names of Ronald E. Swain and Gilbert W. McKenna, and assigned to the present assignee (Attorney's Docket Number ANA-31).

In order to define the fan beam 44 of X-rays photons emanating from the focal spot 42 of the source 40, a primary collimator 60 is disposed between the source 40 and the array of primary detectors 50. The collimator 60 is made of a material impervious to X-rays, such as lead or a lead alloy, and is provided with a narrow slit 62. The length of the slit 62 (the longer dimension) defines in part the angle $\alpha$ subtended by the fan beam around the focal spot 42 (the angle $\alpha$ also being a function of the distance the collimator 60 is placed relative to the focal spot 42), while the width of the slit defines the depth or thickness of the beam passing through the object being scanned, e.g., patient 30, and coincident on the array of primary detectors 50. Ideally, the slit is dimensioned so that the beam is entirely intercepted by the detectors, with the maximum surface area of the detectors 50 being exposed to the X-ray photons.

Figure 2:
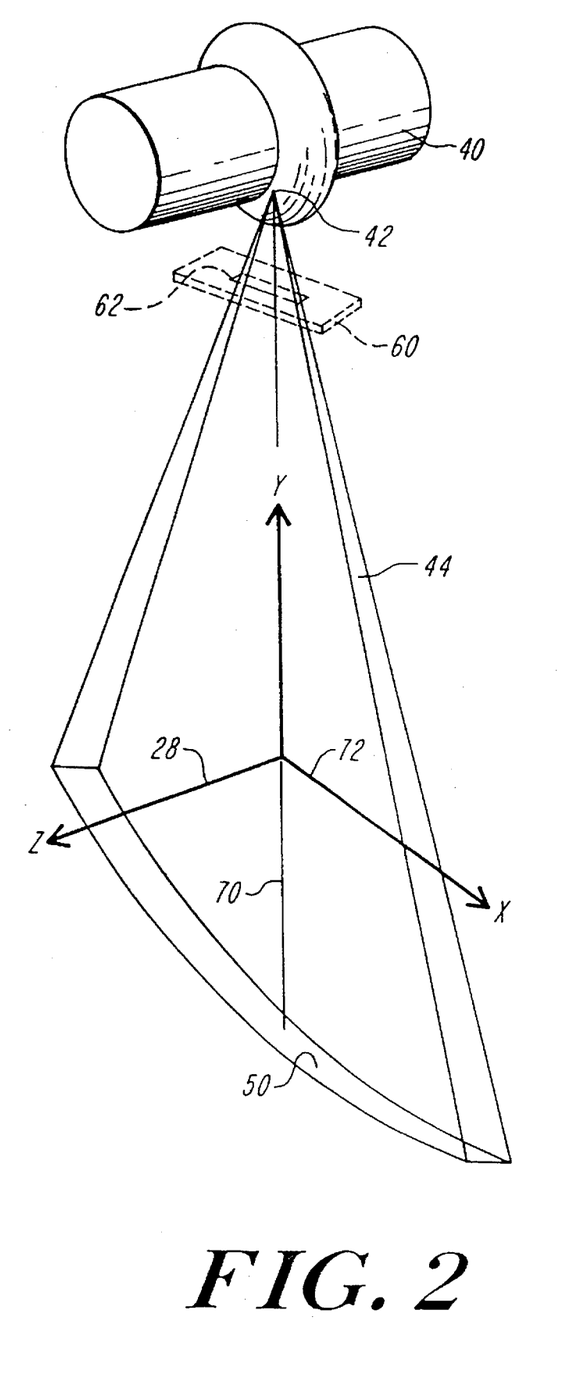
FIG. 2 is an isometric view of a typical source of high energy X-ray photons and the fan beam created by the source and defined by the primary collimator of the apparatus of FIG. 1.

As shown in FIG. 2, the fan beam 44 is produced by an X-ray source 40 and is defined by the slit 62 of the primary collimator 60. The fan beam intersects the detectors of the array so as to define ray paths, with the ray path extending from the focal spot 42 through the Z-axis 28 defining the path of the "center ray". For convenience of exposition, and to facilitate understanding and establish convention, the center ray will be referred to as the "primary axis" or "Y-axis" of the scanning plane, indicated at 70 in FIG. 2, while the X-axis of the scanning plane extends normal to the Y-axis and Z-axis and is identified at 72 in FIG. 2. It should be appreciated that the Y-axis 70 and X-axis 72, which define the scanning plane, to the extent they are used to define the fan beam rotate with the disk 20 of FIG. 1 about the Z-axis 28, and that the Figs. show only one possible rotational position of the disk.

Figure 3:
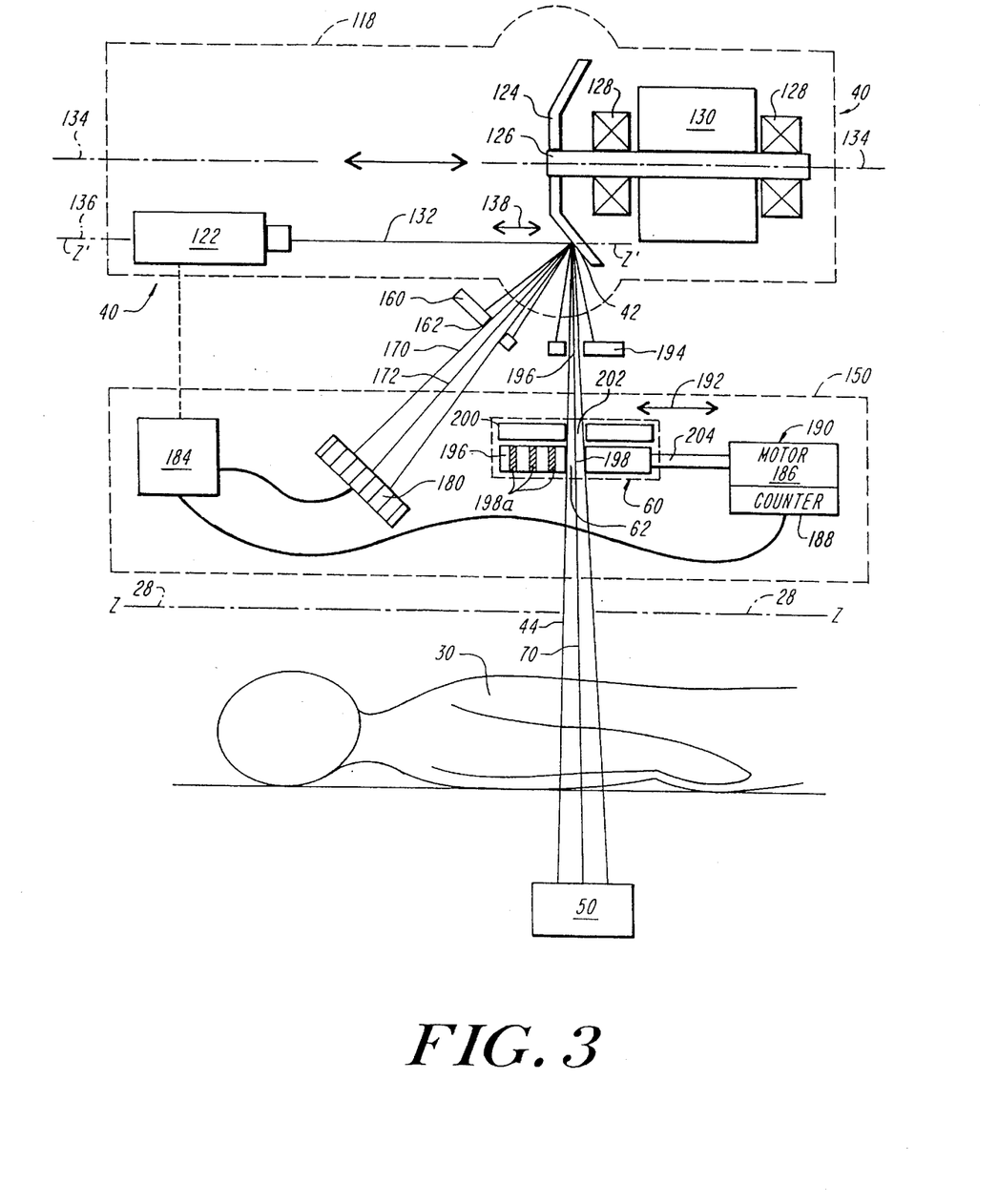
FIG. 3 is a diagrammatic view of the preferred embodiment of the focal spot movement compensation system of the present invention for use in the apparatus shown in FIG. 1.

As shown in FIG. 3, the X-ray source 40 includes an electron beam generator 122, which directs a beam of electrons 132 at an anode 124. Preferably the anode 124 is a tungsten disk, rotatably mounted on a shaft 126, supported by bearings 128 and rotatably driven by motor 130. The anode 124 is rotated to facilitate cooling so as to prevent it from overheating and prevent the electron beam 132 from damaging the anode 124. Typically, the X-ray source 40 is enclosed in an evacuated housing 118 as shown by dashed lines in FIG. 3 and positioned so that the rotation axis 134 of the shaft 126 is parallel to the Z-axis. In the preferred embodiment, the housing 118 is composed of glass and further enclosed in an oil filled aluminum housing (not shown) to facilitate cooling.

Referring still to FIG. 3, the X-ray source 40 produces a primary beam of X-rays that emanate from the focal spot 42 through a port in the housing 118. The slit 62 of primary or slice defining collimator 60 defines and shapes the beam cross-section and directs the primary beam 44 along the primary or Y-axis 70. To the extent thus far described with reference to FIGS. 1–3, the tomography apparatus 12 is known in the prior art. In the prior art the shaft 126 of the source 40 tends to thermally expand due to heat generated by the source as it produces X-rays, and thermally contract when the source stops producing the X-rays and the heat is dissipated. Such thermal expansion and contraction causes the focal spot 42 to shift along an axis, Z'-axis 136, parallel to the Z-axis 28 and the axis 134, resulting in the focal spot 42 moving relative to the slit 62 of the primary collimator 60 as well as the detectors 50, as indicated by the bidirectional arrow 138 shown in FIG. 3. This can produce errors in reading the X-rays with the detectors 50 if the movement of the shaft 126 occurs during a scan, or over the course of many scans since not all of the flux emanating from the focal spot 42 and passing through the slit 62 of the collimator 60 will necessarily be detected by each detector 50 of the detector array because (1) of the resulting spatial misalignment of the focal spot relative to the slit and detector array and (2) of variations in the sensitivity of the detectors 50 in the Z-axis direction.

In accordance with the present invention, a focal spot movement compensation system, indicated generally at 150, is provided to compensate for shifts of the focal spot 42 in a direction parallel to the Z-axis 28 and the Z'-axis 136. The system 150 includes both the primary collimator 60 and a secondary collimator 160 having a slit or aperture 162 for defining, shaping and directing a secondary beam 170 along a secondary axis 172 onto the secondary monitoring device 180 for monitoring the beam 170. As described hereinafter, the secondary monitoring device 180 preferably includes a detector array for providing an output signal as a function of the position of the beam 170. The output of the device 180 is connected to a control system or controller 184 for providing a correction signal as a function of the amount of shift of the focal spot 42 as detected by the device 180. The control system is connected to an actuator device 190 mechanically connected to the primary collimator 60 and adapted to move the collimator so as to move the slit 62 in a direction parallel to the Z-axis 28 and Z'-axis 136, as indicated by the bidirectional arrow 192 shown in FIG. 3. The primary collimator 60 directs the primary beam 44 along the axis 70 through the patient 30 onto the primary detector array 50, as in the prior art, except that the collimator is adapted to bidirectionally move as indicated by arrow 192 so as to maintain the relative alignment of the focal spot 42, slit 60 and detectors 50. Optionally, a precollimator 194 having a slit 196 can be provided to precollimate the primary beam 44 along the axis 70, although it should be appreciated that the slit 196 should be wide enough to allow for movement of the focal spot 42, and therefore the beam 44, and the primary collimator 60 so that the beam 44 is aligned with the primary detector array 50.

In the preferred embodiment, the primary collimator 60, is similar to the primary collimator used in the prior art, and for example comprises a plate of X-ray impervious material, such as a tantalum, on the order of 1 mm thick, having at least one substantially rectangular opening or slit 62 so as to define the fan beam 44 to which the primary detector array 50 is exposed. The primary or slice defining collimator 60 can be adjustable to control the width or "fan out" of the beam and adjustable to control the thickness (Z dimension) of the beam. In the preferred embodiment, the slit 62 of the primary collimator 60 imparts a substantially rectangular shape on the cross-section of the beam 44 in which the width (X dimension) of the beam is several orders of magnitude greater than the thickness (Z dimension) of the beam, particularly at greater distances from the focal spot 42 along the primary axis 70. In this embodiment, it is desirable for the thickness of the beam 44 to be as small as possible to minimize unnecessary X-ray exposure, and large enough to provide sufficient X-rays for a tomographic scan. One method of controlling the thickness of the beam includes sandwiching together tantalum or lead plates to form a shutter and sliding them relative to each other by any suitable means to affect the thickness of the beam. The width or "fan out" of the beam, i.e. angle "α" (shown in FIG. 1), may be controlled in a similar manner.

The primary collimator 60 preferably includes a movable plate 196 provided with a slit 198, and a second plate 200 having single slot 202 fixed relative to the Z-axis, the plates being arranged relative to one another so as to function as a shutter. The slot 202 is much wider than the slit 198 and is sufficiently wide so that the slit can move in either direction of arrow 192 between two extreme locations so that once assembled for operation, the slice of the beam will always be the same and can always be aligned with the detector array 50 regardless of the position of the focal spot 42. The moveable plate 196 is secured in a suitable manner, such as a follower nut of a screw-follower arrangement, which follows a screw, indicated at 204 driven by actuating device 190 so that rotation of the screw causes the plate 196 to translate in a direction parallel to the Z-axis 28, without rotating about the screw. Device 190 preferably includes a motor 186, controlled by a microprocessor in the control system 184. In the preferred embodiment, the actuating device 190 includes a stepping motor where each step corresponds to a different position of the movable plate 196 in one of the directions indicated by bidirectional arrow 192. The total travel of the primary collimator is set to be approximately 0.9375 inches, which corresponds to 2880 steps of the stepping motor, providing translational movement of the plate 196 of only about 0.0003255 inches per step, although these values can vary. Since actual movement of the focal spot in a typical system requires only a small amount of correction by the primary collimator, e.g. about 10 steps of stepping motor 186, or about 0.003255 inches, the plate 198 can be provided with more than one slit 198, such as shown 198A, so that fan beams, i.e., slices of different thicknesses (in the Z-dimension) can be easily provided by moving the desired slit into alignment with the slot 202 with the actuating device 190. The slits are designated by their respective thicknesses of the fan beams they are specified to produce, with the lengths of the slits being all the same in order to expose all of the primary detectors of array 50, and the actual width of each slit being slightly less than its nominal designation due to the spreading of the beam 44. In the preferred embodiment, for example, the slits are 0.1297", 0.0648", 0.0389", and 0.0258" wide to produce 10 mm, 5 mm, 3 mm and 2 mm thick beams, respectively.

In addition to the stepping motor 186, the actuating device 190 also preferably includes a counter 188 for keeping track of the steps, and thus the position of the plate 196. The counter is connected to and communicates with the microprocessor provided in the control system 184.

Figure 4:
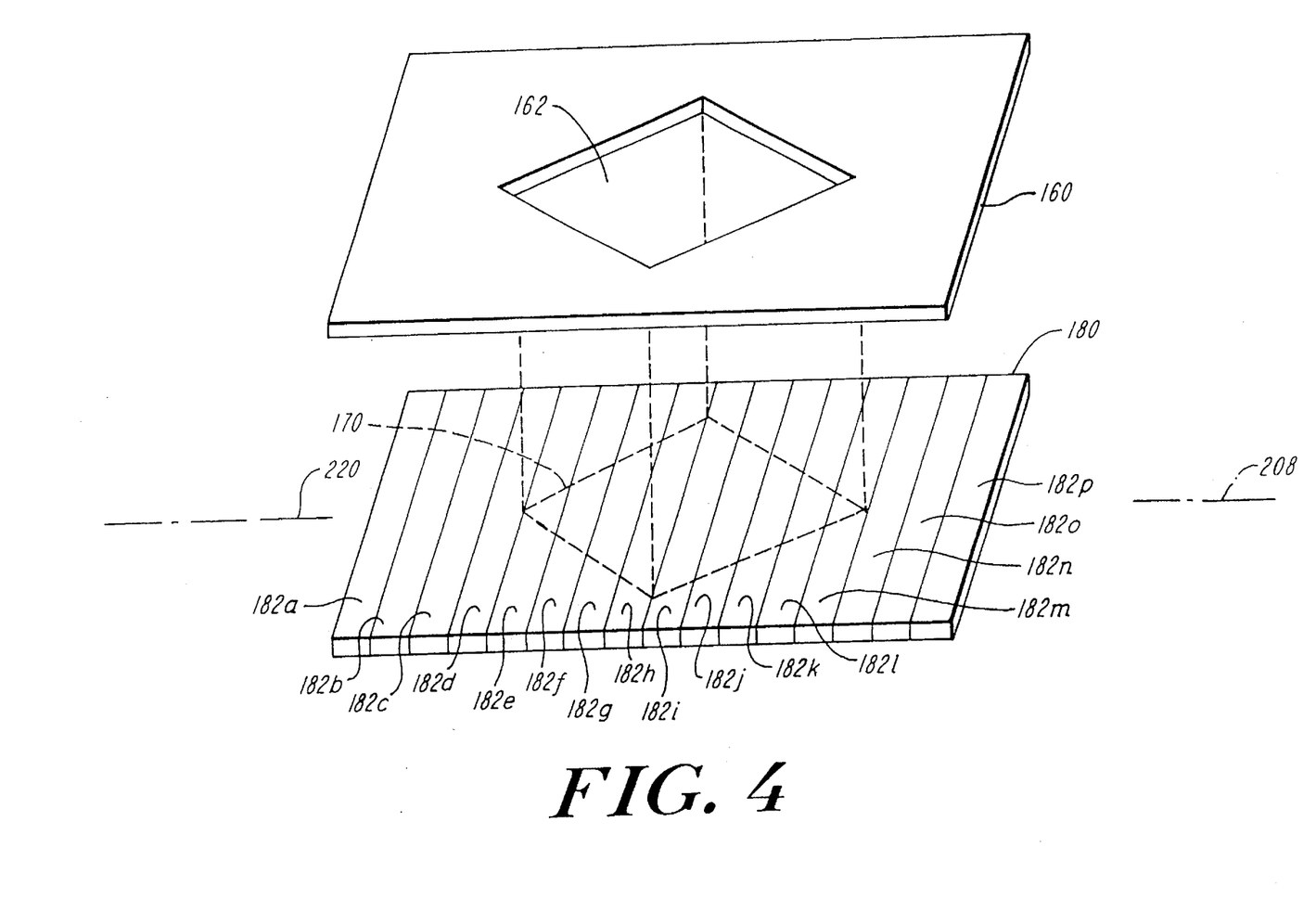
FIG. 4 is an isometric view of one secondary collimator and the detector array of the preferred secondary X-ray monitoring device of the focal spot movement compensation system shown in FIG. 3 and arranged in accordance with the present invention.
Figure 5:
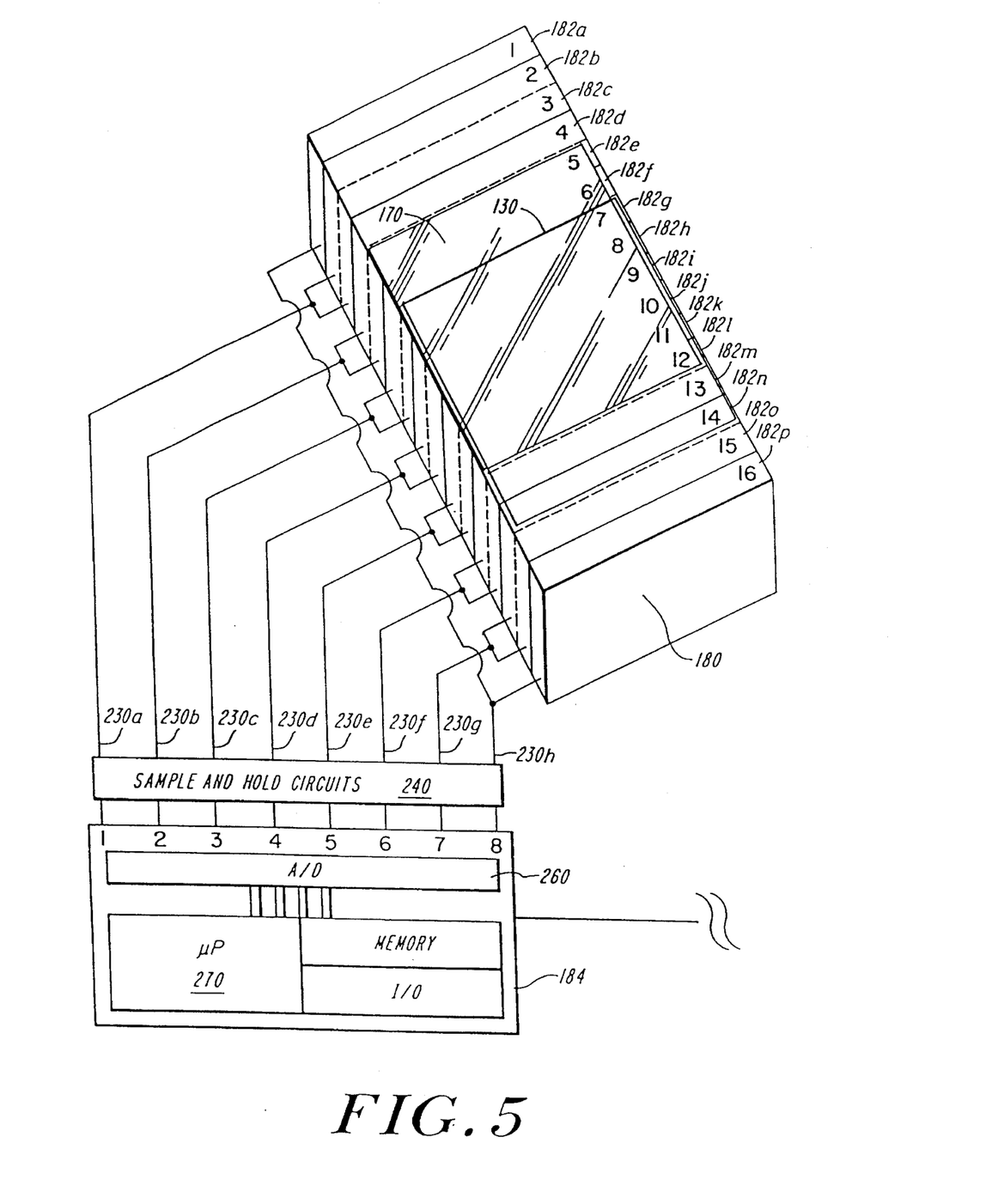
FIG. 5 is a diagrammatic view of the preferred embodiment of the secondary monitoring device.

As shown generally in FIG. 3, and in greater detail in FIGS. 4 and 5, the secondary beam 170 is directed through the secondary collimator 160 onto the secondary monitoring device 180. The secondary collimator 160 is also made of an X-ray impervious material, such as a 1 mm thick plate of tungsten or tantalum, preferably having at least one geometric shaped opening for defining the aperture 162. The precollimator 194, if used, may be integral with the secondary collimator 160 or a separate component. It is preferable that both the precollimator 194 and the secondary collimator 160 be as close to the focal spot 42 as possible and that the primary collimator 60 be as far from the focal spot 42 as space allows. The secondary collimator 160 includes the aperture 162 shaped so that the secondary beam 170 has a predetermined geometric cross-section. The geometric pattern, for example, can be rhomboidal or diamond shaped as shown in FIG. 4, or rectangular or square as suggested in FIG. 5. The secondary monitoring device 180 preferably comprises a plurality of X-ray detectors arranged in a stacked array as best seen in FIGS. 4 and 5. In particular, the detectors are arranged in a linear array extending along a longitudinal axis indicated at 208. Each detector of the array includes a detecting surface and the detectors of surfaces of the detectors are all in a common plane parallel to or coplanar with the longitudinal axis 208. As shown in the drawing, sixteen detectors, indicated at 182a–182p, are used in the preferred system. The secondary monitoring device 180 is oriented such that any movement of the focal spot 42 along the Z'-axis causes the secondary beam 170 to move along a path along the longitudinal axis 208, transversely crossing the detectors in the stacked array as indicated by the bidirectional arrow 220. The output of each detector 182a–182p is proportional to the magnitude of the X-ray flux incident upon the detector during each projection view. As shown in FIGS. 4 and 5, the preferred embodiment contemplates the detector array 180 consisting of 16 individual detectors. The outer most detectors 182a and 182p function as guard detectors. The secondary monitoring device 180 is positioned such that over the expected range of movement of the focal spot 42, the beam 170 will not fall on either guard detector 182a and 182p. This provides a margin of safety because if radiation is sensed by either of the guard detectors 182a or 182p, its output signal would be greater than zero and a malfunction would be presumed to exist. This condition causes the control system 184 to produce a signal shutting down the source 40 and indicating to the operator by any suitable means, such as an alarm or a monitor (not shown) used to view the reconstructed image, that an error exists. Under these circumstances the outputs of guard detectors 182a and 182p can be summed together and processed through a single line 230h, as indicated in FIG. 5. The remaining intermediate detectors 182b–182o are grouped into adjacent pairs forming detector channels 230a–230g, i.e., adjacent pairs of detectors 182b and 182c, 182d and 182e, 182f and 182g, 182h and 182i, 182j and 182k, 182l and 182m, and 182n and 182o are connected together as seen in FIG. 5 so that the output signals of each of the detectors of each pair are summed together and transmitted through lines 230a–230g. This results in eight pairs of detectors producing eight output signals. The output of each pair is summed together and fed into the control system 184. As indicated in FIG. 5, the control system 184 preferably includes means, for example in the form of sample and hold circuits indicated at 240, for sampling the analog signal provided over each line 230a–230h during predetermined intervals. The sample and hold circuits can each provide an output to an analog to digital (A/D) converter 260 for converting each analog signal to a digital value. Where only one A/D converter is used for the eight sample and hold circuits, a multiplexer (not shown) is used for sequentially applying the sampled signals to the single A/D converter, a technique which is well known.

The preferred control system 184 also includes a microprocessor 270 with associated memory and input/output subsystems for controlling the components of system 184 as well as the actuating device 190, and for storing data.

In order to accurately determine whether and to what extent the focal spot 42 has shifted in the direction of the Z'-axis, and therefore has shifted relative to the primary collimator 60 and primary detector array 50, any movement of the secondary beam 170 transversely on the detectors 182 of the secondary monitoring device along the longitudinal axis 208 in either direction of the bidirectional arrow 220 must be precisely measured. The shape of the secondary beam cross-section, as prescribed by the aperture 162, determines the nature of interrelationship among the output signals from the detectors 182 of secondary monitor device 180. The shape can be chosen to emphasize the minimum amount of movement of the focal spot detected by the device 180 for which compensation is desired. In preferred embodiment, the secondary beam 170 is given a square shape to enhance the differences between one channel receiving a signal representing full exposure and the one receiving partial exposure at the edge of the beam.

Figure 6:
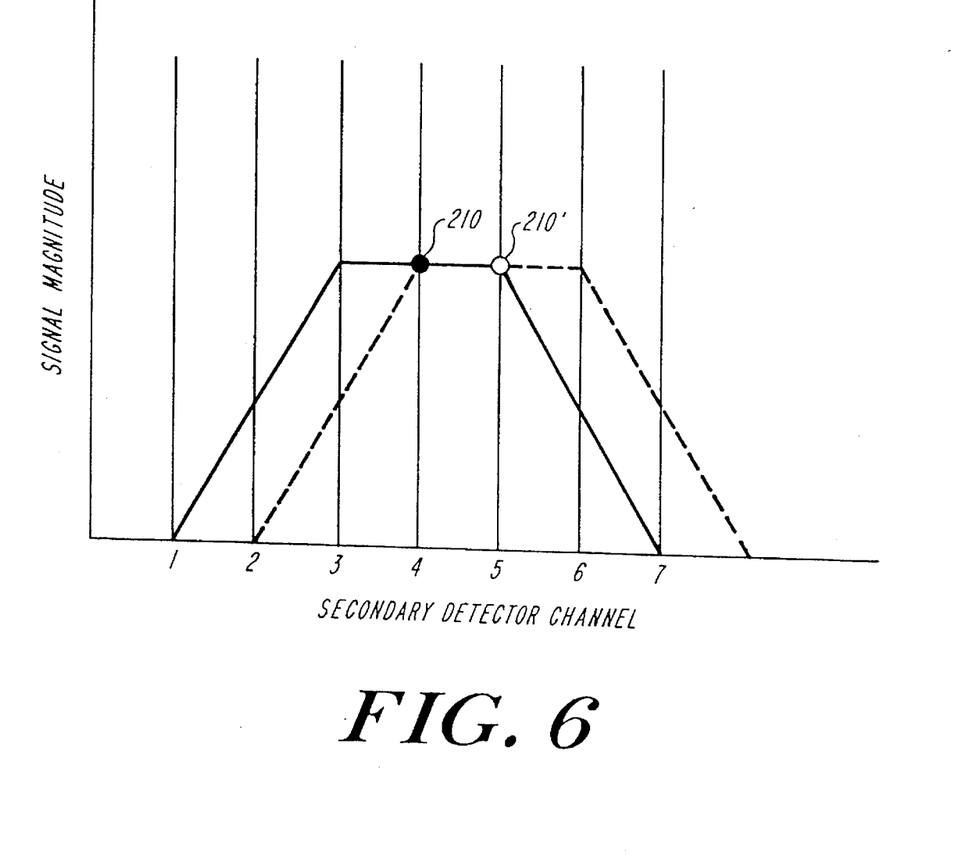
FIG. 6 is a graph illustrating the relationship between the signal output of the secondary monitoring device and the position of the secondary X-ray beam on the detector array of the focal spot movement compensation system of the present invention.

As shown in FIG. 5, when the aperture 162 is rectangular the beam 170 is given a substantially rectangular cross-section which produces a set of output signals which is trapezoidal in shape, as shown in FIG. 6. The width of the beam (in a direction perpendicular to axis 208) extends across the entire length of the detectors so as to maximize the use of each detector, while the length of the beam is approximately equal to the width of eight detectors or four channels. The beam is preferably, although not necessarily, substantially centered with respect to the two center detectors 182i, 182j when the beam and detectors are properly aligned. When the secondary beam moves along the axis 208, the trapezoidal shaped output response illustrated in FIG. 6 tends to shift left or right as indicated in the Fig. The system is designed so that the maximum movement of the focal spot along the Z'-axis is such that the maximum anticipated travel of the secondary beam 170 on the secondary monitor device 180 is approximately ½ of a detector width or ¼ of a channel.

Alternatively, the beam can be other cross-sectional shapes, such as a rhomboid or diamond, which when the beam 170 is properly aligned with the detector monitoring device 180, produces the largest output signal from the pair of center detectors 182h and 182i, substantially equal, but smaller output signals from the pairs of adjacent detectors 182f, 182g and 182j, 182k, substantially equal, but even smaller output signals from the pairs of adjacent detectors 182d, 182e and 182l, 182m, and substantially equal and yet even smaller output signals from the pairs of adjacent detectors 182b,182c and 182n, 182o, which when graphically illustrated resembles a triangle which shifts relative to the channels when the beam shifts along axis 208.

In the preferred embodiment, where the degree of desired detectable shift of the beam 170 is much less than the distance between the pairs of the detectors in the array, the movement of the secondary beam is determined as a function of, and in particular by the degree of detectable shift of the center of the beam, which is the centroid 210 of the output signals as, for example, depicted FIG. 6. The centroid can be interpolated from the individual output signals of the detectors. In the preferred embodiment, the centroid or position of the of the beam is determined as the average position (the abscissa) along the horizontal-axis of the curve illustrated in FIG. 6, and given by the following equation:

$$C = \frac{\sum_{c=1}^{n} N_c V_c}{\sum_{c=1}^{n} V_c} \quad (1)$$

where

C is the centroid or center of the beam, $N_c$ is the channel number, $V_c$ is the signal value for the channel, and n is the number of channels (7 in the preferred embodiment) receiving signal information.

The sum of the outputs of all of the detectors 182a–182p corresponds to the magnitude of the total radiation incident upon the detector array. This value can be fed back to the X-ray source 40 and used to control the level of the radiation output to ensure substantially constant X-ray levels for all of the projection views of a scan. Alternatively, the incident radiation value data can be used with the projection view data as a basis to normalize the projection views, as described in copending application U.S. Ser. No. 08/343,248, filed in the names of John Dobbs and Hans Weedon, entitled X-ray Image Data Normalization in a CT Scanner, and assigned to the present assignee (Attorney's Docket Number ANA-60).

In operation, the X-ray source 40 is operated over a temperature range that begins at approximately 600 degrees Celsius and ends at approximately 1500 degrees Celsius. During that thermal cycle, the materials in the X-ray source 40 are influenced by thermal expansion and cause the position of the focal spot 42 to move along the Z'-axis 136. This results in the primary beam 44 effectively pivoting about the aperture 62 of the primary collimator 60 so as to shift along the Z axis and either partially or completely miss the primary detector array 50 and significantly degrade or interrupt the performance of the tomography system. When a shift in the centroid is detected by the device 184 a signal is provided to the stepping motor 190 so as to move the primary collimator 60 an appropriate amount in order to shift the primary beam 44 and axis 70 an appropriate amount. To compensate for the focal spot shift, the primary collimator 60 is shifted an analogous amount in the Z direction to redirect the primary beam 70 onto the center of the primary detector array 50.

In order to effectively compensate for the focal spot shift, the system must be initially calibrated. The relationship among the focal spot shift, the shift of the secondary beam 170 movement on the secondary detectors 182 of the secondary monitoring device 180, and position of the primary collimator 60 can be derived numerically from the known geometric relationship among the relative positions of the focal spot 42, the primary collimator 60, the secondary collimator 160 and the secondary monitoring device 180. In the preferred embodiment, the calibration is done empirically. With the X-ray source 40 cold (approx. 600° C.) and no patient or object positioned in the machine, the primary collimator 60 is moved and for each step of the motor 190 or position of the primary collimator 60, the output of primary detectors 50 and the output from the secondary detectors 182 of the secondary monitoring device 180 is recorded. The maximum signal output of the primary detectors 50 is the optimum position for the collimator 60. At that position the centroid position of the signals detected from the device 180, as calculated in accordance with equation (1) above, is the home position of the secondary beam 170 for the measured focal for a cold anode.

The X-ray tube is then heated to 95% of the maximum temperature (approx. 1500° C.) producing substantially the maximum shift of the focal spot 42 along the Z'-axis 136. At this position the output of the detectors 182 of the secondary monitoring device 180 are processed and the corresponding secondary detector centroid calculated in accordance with equation (1) to determine the corresponding change in the value of the centroid. The change in the value of the centroid as a function of the change in the shift of the position of the primary collimator 60 necessary to shift the fan beam back to a position where maximum exposure of the primary detector array 50 occurs is determined from the following equation:

$$M = \frac{(ST_H - ST_C)}{(C_H - C_C)} \quad (2)$$

wherein

M is the slope or rate of change between the position of the primary collimator and the value of the centroid value determined by the secondary monitoring device 180 and control 184;

$ST_H$ is the position of the primary collimator in steps (as measured by the counter 188) when the X-ray tube is hot;

$ST_C$ is the position of the primary collimator in steps (as measured by the counter 188) when the X-ray tube is cold;

$C_H$ is the centroid value determined by the secondary monitoring device 180 and control 184 corresponding to $ST_H$;

$C_C$ is the centroid value determined by the secondary monitoring device 180 and control 184 corresponding to $ST_C$.

Ordinarily, the slope M is calculated when the machine is initially assembled and it is not necessary to recalculate it unless one of the parts, i.e., the source 40, primary collimator 60, secondary collimator 160, primary detector array 50 or secondary detector array 180, is positionally adjusted or replaced by a technician. The values can be stored in microprocessor 270. Where plate 196 of the primary collimator 60 has more that one slit, the values for each slit can also be stored in the memory of microprocessor 270.

The primary collimator can thus be adjusted based on the slope M and the cold center position $ST_C$ of the primary detector and the corresponding centroid value $C_C$. The step for a given centroid is determined from the following equation:

$$ST = M(C_C - C) + ST_C \quad (3)$$

where

ST is the new step position as determined by the counter 188 for positioning the primary collimator 60;

M is the slope determined from equation (2);

$C_C$ is the centroid determined by the secondary monitoring device 180 and control 184 when the source 40 is cold;

C is the centroid value determined by the secondary monitoring device 180 and control 184 for the current focal spot position;

$ST_C$ is the step position as determined by the counter 188 when the X-ray tube is cold.

Using equation (3), the new step position ST can be calculated each time a movement of the secondary beam on the secondary detector 180 is detected. In the preferred embodiment, equation (3) is used to produce a lookup table including a centroid value for each step, the lookup table being stored in the memory of microprocessor 270. Where the primary collimator 60 includes more than one slit, a separate lookup table can be provided and stored.

In operation, the control system 184 reads the signals from the individual detectors 182b–182o at predetermined intervals and determines the amount of positional shift of the focal spot 42. The control system 184 then determines (by calculation or table lookup) the positional displacement of the primary collimator 60 necessary to redirect the primary beam 44 onto the center of the primary detector array 50. The controller 184 generates a control signal and transmits it to the stepping motor 190 which moves the plate 196 of the primary collimator 60 the predetermined amount.

In one preferred embodiment, the primary collimator 60 is approximately 15 cm from the focal spot 42 and the primary detector array is approximately 0.845 m from the focal spot 42. Thus, a 3 mm shift in the focal spot 42 will result in a 1.7 mm shift of the beam on the primary detector array 50. To compensate for this, the plate 196 of primary collimator 60 is provided with a minimum movement of 0.25 mm to keep the beam positioned on the primary detector array 50.

The invention therefore provides an improve tomography system by providing a more positionally stable beam of high energy X-ray photons. The focal spot movement compensation system 150 compensates for misalignment of the focal spot 42 of the source 40 relative to the collimator 60 and detectors 50 due to Z-axis beam shifting so as to provide more accurate scan data. By compensating for Z-axis focal spot shift, and maintaining the positional stability of the beam on the detectors 50, errors in X-ray flux measurements due to the variation of detector sensitivity in the Z-axis direction will be reduced.

While the invention has been specifically described in the context of a third generation CT scanner, it will be evident that the invention can be employed in other types of CT scanners, such as fourth generation machines.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A system for controlling the direction of a fan beam of X-radiation, produced at the focal spot of an X-ray source of a tomography system and directed toward a detector array of X-ray detectors of the tomography system, said system comprising:

(a) fan beam defining means including a fan beam collimator, positionable between the focal spot and at least some of the detectors of the array, for defining said fan beam; and (b) means for defining a secondary beam of X-radiation, produced at the focal spot of the X-ray source at the same time as the fan beam, and directed transversely to the fan beam;

(c) means, responsive to said secondary beam of X-radiation, for detecting a shift of the focal spot in a direction parallel to the Z-axis of the tomography system and for generating a control signal as a function of the amount of said shift; and (d) means, responsive to the control signal, for moving the fan beam collimator so as to maintain an alignment between said fan beam and said detectors.

2. A system according to claim 1, wherein said means for detecting a shift of the focal spot and for generating the control signal comprises (a) target means for receiving X-radiation from said secondary beam, and for generating a signal representative thereof, and (b) means for defining a secondary collimator, positionable between the focal spot and said target means, for defining said secondary beam of radiation, said secondary beam being directed from the focal spot onto the target means so that movement of said focal spot in a direction parallel to the Z-axis shifts said secondary beam of radiation on said target means.

3. A system according to claim 2, wherein said target means comprises a second array of detectors, positionable relative to said focal spot so that shifting of said focal spot in a direction parallel to the Z-axis shifts said secondary beam of radiation transversely to said second array.

4. A system according to claim 3, wherein said second array of detectors are positionable relative to said focal spot so that shifting of said focal spot in a direction parallel to the Z-axis shifts said secondary beam of radiation perpendicularly to said second array.

5. A system according to claim 3, wherein the detectors of the second array each generates a detection signal as a function of the radiation portion of the secondary beam detected by the detector, and said means for detecting a shift of the focal spot and for generating a control signal further comprises means for processing the detection signals received from at least some of said detectors of said second array so as to determine the position of the center of said secondary beam and for generating said control signal as a function of said position.

6. A system according to claim 3, wherein the detectors of the second array each generates a detection signal as a function of the radiation portion of the secondary beam detected by the detector, and said means for detecting a shift of the focal spot and for generating a control signal further comprises means for processing the detection signals received from at least some of said detectors of said second array so as to determine a centroid value of the detection signals as a function of the relative position of each of said detectors and the value of each detection signal, and for generating said control signal as a function of said centroid value.

7. A system according to claim 6, wherein said means for generating said control signal includes means for processing the detection signals through a plurality of channels, and the centroid value is determined by the following equation:

$$C = \frac{\sum_{c=1}^{n} N_c V_c}{\sum_{c=1}^{n} V_c}$$

where

C represents the centroid value of the beam, $N_c$ is the channel number, $V_c$ is the signal value for the channel, and n is the number of channels receiving signal information.

8. A system according to claim 3, wherein said second array of detectors includes two detectors disposed at opposite ends of the array for providing a failure signal should either of said two detectors detect at least a portion of the secondary beam.

9. An improved tomography system comprising:

a source for generating radiation from a focal spot;

means for rotating said source about a Z-axis during a tomographic scan;

a primary array of detectors for receiving radiation from the source during a tomographic scan;

primary collimating means, positioned relative to the focal spot, for collimating radiation emanating from the focal spot so as to define a primary beam of radiation propagating from the focal spot onto the detectors of said primary array during a tomographic scan so as to define a fan beam;

means for defining a secondary beam of radiation propagating from the focal spot at the same time as the fan beam, and directed transversely to the fan beam;

means, responsive to a secondary beam of radiation, for sensing the position of the focal spot and for generating a position signal as a function of the position of said focal spot; and means, responsive to the position signal, for moving said primary collimating means so as to maintain an alignment of said primary beam of radiation and the detectors of the primary array.

10. A system according to claim 9, wherein said means for sensing the position of the focal spot and for generating a position signal comprises target means for receiving X-radiation from said secondary beam and for generating a signal representative thereof, and said means for defining a secondary beam includes a secondary collimator, positioned between the focal spot and said target means, for defining said secondary beam of radiation, said secondary beam being directed from the focal spot onto the target means so that shifting of said focal spot shifts said secondary beam of radiation on said target means.

11. A system according to claim 10, wherein the primary beam of radiation is disposed substantially within and defines the scanning plane of the tomography system wherein the Z-axis is substantially normal to said scanning plane, and said secondary beam extends along an axis transverse to said scanning plane.

12. A system according to claim 9, wherein said means for sensing the position of the focal spot and for generating the position signal comprises target means for receiving X-radiation from said secondary beam and for generating a signal representative thereof, and said means for defining a secondary beam includes a secondary collimator, positionable between the focal spot and said target means, for defining a secondary beam of radiation, said secondary beam being transverse to the scanning plane of the tomography system and being directed from the focal spot onto the target means so that movement of said focal spot in a direction parallel to the Z-axis shifts said secondary beam of radiation on said target means.

13. A system according to claim 12, wherein said target means comprises a second array of detectors, positionable relative to said focal spot so that shifting of said focal spot in a direction parallel to the Z-axis shifts said secondary beam of radiation transversely to said second array.

14. A system according to claim 13, wherein said second array of detectors are positioned relative to said focal spot so that shifting of said focal spot in a direction parallel to the Z-axis shifts said secondary beam of radiation perpendicularly to said second array.

15. A system according to claim 13, wherein the detectors of the second array each generates a detection signal as a function of the radiation portion of the secondary beam detected by the detector, and said means for detecting a shift of the focal spot and for generating a control signal further comprises means for processing the detection signals received from at least some of said detectors of said second array so as to determine the position of the center of said secondary beam and for generating said control signal as a function of said position.

16. A system according to claim 13, wherein the detectors of the second array each generates a detection signal as a function of the radiation portion of the secondary beam detected by the detector, and said means for detecting a shift of the focal spot and for generating a control signal further comprises means for processing the detection signals received from at least some of said detectors of said second array so as to determine a centroid value of detection signals as a function of the relative position of each of said detectors and the value of each detection signal, and for generating said control signal as a function of said centroid value.

17. A system according to claim 16, wherein said means for generating said control signal includes means for processing the detection signals through a plurality of channels, and the centroid value is determined by the following equation:

$$C = \frac{\sum\limits_{c=1}^{n} N_c V_c}{\sum\limits_{c=1}^{n} V_c}$$

where

C represents the centroid value of the beam, $N_c$ is the channel number, $V_c$ is the signal value for the channel, and n is the number of channels receiving signal information.

18. A system according to claim 13, wherein said second array of detectors includes two detectors disposed at opposite ends of the array for providing a failure signal should either of said two detectors detect at least a portion of the secondary beam.

19. A system according to claim 12, wherein said target means includes: a plurality of detector elements arranged in a linear array extending along a longitudinal axis, and said plurality of detector elements are arranged relative to said focal spot so that movement of said focal spot in a direction parallel to the Z-axis shifts said secondary beam substantially parallel to said longitudinal axis.

20. A system according to claim 19, wherein each said detector element includes a detecting surface and each said detecting surface is arranged in a linear array along said longitudinal axis and lies in a common plane transverse to said secondary axis and said secondary beam.

21. A system according to claim 20, wherein each said detecting element has an output for transmitting a corresponding position signal to said means for moving said primary collimator means, and said linear array has two ends and the outputs of the detecting elements at each said end of said linear array are summed together and the outputs of adjacent pairs of detecting elements between said ends are summed together.

22. A system according to claim 20, wherein said detecting means includes sixteen detecting elements in said linear array.

23. A system according to claim 22, wherein each said detecting element has an output for transmitting said position signals to said means for moving said primary collimating means, and the linear array has two ends and the outputs of the detecting elements at each said end of said linear array are summed together and the outputs of adjacent pairs of detecting elements between said ends are summed together so as to form eight output channels.

24. A system according to claim 9, wherein said means, responsive to the position signal, for moving the primary collimating means so as to maintain the alignment of said primary beam of radiation and the detectors of the primary array includes processing means, including a lookup table means, for storing data relating to the value of said position signal with the position of said primary collimating means.

25. A system according to claim 9, wherein said primary collimator means includes a plurality of slits for defining a corresponding number of different primary beams of radiation, and said means for moving said primary collimating means includes means for selectively moving each of said slits into alignment with said focal spot and primary array of detectors.

* * * * *